United States Patent [19]

Merrill et al.

[11] Patent Number: 4,529,880

[45] Date of Patent: Jul. 16, 1985

[54] METHOD FOR TESTING DETERGENT PERFORMANCE

[75] Inventors: Connie L. Merrill; Andrea Sanders, both of Houston, Tex.

[73] Assignee: Shell Oil Company, Houston, Tex.

[21] Appl. No.: 484,754

[22] Filed: Apr. 14, 1983

[51] Int. Cl.³ .............................................. G01T 1/161
[52] U.S. Cl. .................................................... 250/303
[58] Field of Search ................................. 250/302, 303

[56] References Cited

U.S. PATENT DOCUMENTS 4,259,215 3/1981 Chiba et al. ......................... 252/528

OTHER PUBLICATIONS

The Development of a Particulate Radioactive Soil for Detergency Studies, B. E. Gordon and E. L. Bastin, J. Am. Oil Chem. Soc., vol. 45, pp. 754–759, Nov. 68.
Double Label Radiotracer Approach to Detergency Studies, Gordon J. Roddewig and W. T. Shebs, J. Am. Oil Chem. Soc., vol. 44, pp. 289–294, May 1967.
Improvements in Detergency Precision with Radioactive Soil, W. T. Shebbs and B. E. Gordon, J. Am. Oil Chem. Soc., vol. 45, pp. 377–380.
A Triply Labeled Particulate Soil for Detergency Studies, B. E. Gordon and W. T. Shebs, J. Am. Oil Chem. Soc., vol. 46, pp. 537–543.

*Primary Examiner*—Bruce C. Anderson

[57] ABSTRACT

A reliable method for testing the performance of detergent compositions, particularly from the standpoint of the redeposition of soils on fabrics during the laundry wash cycle, which comprises subjecting a clean control fabric swatch to multiple washings, each washing conducted in a solution of the detergent composition and in the presence of one or more pre-soiled fabric swatches, and then analyzing the control swatch for soil content, for example, by light reflectance or radiotracer methods.

6 Claims, No Drawings

4,529,880

METHOD FOR TESTING DETERGENT PERFORMANCE

BACKGROUND OF THE INVENTION

This invention relates to a method for the testing of laundry detergent performance, more particularly to a method for simultaneously determining both the removal and subsequent redeposition of soils on fabrics during the laundry wash cycle.

At present there is great interest in the detergent industry in compositions for laundry applications which combine surfactants responsible for effective cleaning with additives which impart fabric softening and antistatic effects. Compositions of this type are described, for instance, in U.S. Pat. Nos. 4,058,489, 4,259,215, 4,264,457, 4,333,862, Japanese Pat. No. J55058257, and published patent application Ser. No. 2,054,635 of the United Kingdom.

It is known that the softening and antistatic properties of such detergent and fabric softener combination products are the result of the coating or deposition of the additive onto the fabric surface during the wash cycle. Also during the wash cycle, of course, tne detergent components of the composition must function to remove soils from the fabric and suspend them in the wash water. Not surprisingly, it is found that in coating the fabric the softening and antistatic additives may interfere with removal of soils from the fabric and/or cause the redeposition onto the fabric of soils which had previously been removed.

There is a need in formulating detergent compositions generally, and combinations of detergent and fabric softener in particular, to be able to distinguish between the soil removal capabilities of the detergent components and any interference with detergent action which may result from the use of the fabric softener. It is the object of this invention to provide a test method capable of the desired distinction.

One method has been proposed in the art for measuring "recontamination" of fabric during washing with fabric softening detergent products. The aforementioned U.S. Pat. No. 4,259,215 describes a test in which carbon black is ultrasonically dispersed in a solution of the detergent product in water. Clean cloth swatches are then washed in the dispersion. After washing, the swatches are evaluated to determine if they are darker then the original clean swatches. Although this patent points out the need for a soil redeposition test, the method which it describes for this purpose fails to fully satisfy that need in several respects. For example, the method of the patent does not measure recontamination or redeposition in literal terms, since the soil is initially present not on soiled fabric but in a controlled dispersion. For this same reason, the test is unable to simultaneously measure both soil removal and soil redeposition during the same wash cycle. Furthermore, the test as applied in the patent is qualitative rather than quantitative, and does not yield the type of result necessary for use in programs aimed at formulating products exhibiting optimum performance. Still further, this method of the prior art is limited to one type of soil. A full understanding of detergent performance requires the testing of a variety of soil types and/or mixtures of different soils.

SUMMARY OF THE INVENTION

The present invention provides a method for determining the performance of detergent compositions and is particularly useful in investigating soil redeposition aspects of such performance. This method is generally characterized by close simulation of soil removal and redeposition under typical wash conditions, by broad applicability to various soils and fabrics, and by reliable test results from the standpoint of both quantitative measurement of soil redeposition and ranking of the effectiveness of different detergent compositions in minimizing redeposition.

The invention centers on multiple washings of at least one initially clean control (or redeposition) fabric swatch, each such washing conducted in a solution of the detergent composition under evaluation and in the presence of one or more pre-soiled fabric swatches. In the course of the washings, soil is both removed from and redeposited on the fabric present. Following the washings, soil redeposition is determined by analysis of the control swatch for soil content, for instance, by light reflectance or radiotracer techniques. In practice, reliability of test results is found to be critically dependent upon multiple washings of the control swatch, upon the use of fresh detergent solution and soiled fabric in each wash, and upon the quantity of soil available for redeposition relative to the quantity of control fabric.

More specifically, the invention may be described in summary as a method for testing the performance of a detergent composition which comprises steps for a. washing in a first wash cycle and in a first solution of the detergent composition at least one clean control fabric swatch in the presence of a soiled fabric containing a total of at least about 150 mg soil per liter of said first solution, b. separating the control swatch from the first wash cycle, c. washing the control swatch in a second wash cycle and in a second solution of the detergent composition in the presence of soiled fabric containing a total of at least about 150 mg soil per liter of said second solution, d. separating the control swatch from second wash cycle, and e. quantitatively measuring the soil content of the control swatch.

Additional wash cycles, performed between steps (d) and (e), each such cycle using fresh detergent solution and soiled swatches having the indicated total soil content, further enhance the reliability of the test results.

DESCRIPTION OF THE PREFERRED EMBODIMENTS

The invention is broadly applicable to the testing of the soil removal and redeposition performance of essentially any detergent composition which might be considered for use in home or commercial laundry. It is particularly useful in evaluating compositions which combine detergent and fabric softening components such as, for instance, the products disclosed in the above referenced patents which combine nonionic and anionic surfactants for detergency with cationic surfactants for fabric softening.

Similarly, the invention is broadly applicable to different soil and fabric types. As examples of the fabrics which can be used, either as the control fabric or the pre-soiled fabric, mention may be made of cotton, polyester, nylon, dacron, and mixtures thereof. Before use in the invention, fabric swatches are preferably treated, for instance by a thorough washing to remove sizing or other substances which may remain on the fabric surface as the result of its manufacture. Preference may be stated for use of cotton or combination polyester and cotton fabric swatches. On the one hand, the polyester/cotton fabric (for example 65% polyester/35% cotton) is preferred for simulation of the most typical laundry fabric. On the other hand, the replication of data and the discrimination of results between different detergent formulations are usually superior for tests using cotton swatches. Swatches of a size about 4" square are very convenient for purposes of this invention.

For preparation of the pre-soiled swatches, it is preferred that a synthetic soil, of controlled composition, be applied to the fabric under controlled conditions. Particularly suitable radiolabeled synthetic soil compositions and methods for their application are described, for instance, in the Journal of the American Oil Chemists Society (JAOCS), vol. 45, p. 289 (1967); JAOCS, vol. 45, p. 377 (1968); JAOCS, vol. 45, p. 754 (1968); and JAOCS, vol. 46, p. 537 (1969). Mixtures of carbon black with other soils, for instance, mineral oil and carbon black mixtures, have proved very useful for tests in which soil redeposition is determined by light reflectance measurement.

In conducting the several wash cycles of the control fabric swatch (or swatches) with the one or more pre-soiled swatches, attention should be given to controlled conditions of wash water hardness, temperature, and detergent content as well as to the extent of the agitation of the wash mixture. While control over such variables in any one test is necessary for reliable results, it is of advantage that the invention can be applied in a series of tests to independently assess the influence on soil redeposition of variations in such conditions.

It has been found particularly important in the practice of the invention that the control fabric swatch be subjected to at least two wash cycles, each conducted in fresh detergent solutions and in the presence of fresh pre-soiled swatches. A single wash cycle fails to provide the desired reliability for soil redeposition test results. A number of wash cycles in the range from 2 to 10 is preferred, while 3 to 5 cycles is considered most preferred.

Another factor critical to the successful application of the invention is the quantity of soil made available in the wash cycle for redeposition onto the control swatch. As a rule, the pre-soiled swatches added to each wash cycle suitably contain a total quantity of soil that is at least about 150 mg for every liter of wash water solution, and preferably contain greater than about 200 mg of soil for every liter of wash solution. Particularly good results are obtained with soiled swatches containing a total of between about 200 mg and 300 mg of soil for every liter of wash solution.

Each cycle is preferably, but not necessarily, conducted using between about 0.2 and 0.5 g of detergent formulation per liter of wash solution. Preference may also be stated for a total quantity of fabric, (control plus pre-soiled fabric) relative to wash solution, that is between about 8 g and 20 g fabric per liter of solution, particularly between about 10 g and 15 g fabric per liter of solution.

Analyses of the combined wash water solutions and/or of the pre-soiled swatches after use in the wash cycles permits a determination of the total soil available for redeposition. Effectiveness of different detergent formulations in minimizing redeposition can then be determined as a direct function of the quantity of soil redeposited relative to that available for redeposition.

Following completion of the desired number of wash cycles, the control swatch is analyzed for soil redeposition. One preferred method for such analysis involves the use of a white cloth control swatch and measurement of its light reflectance before and after the soil redeposition test. The degree of whiteness retained by the control swatch after the test is indirectly proportional to the amount of soil deposited on the swatch. Another, particularly preferred analysis method involves the use of radiolabeled soils in the soiling of the pre-soiled swatches. Following the completion of the wash cycles, soil content of the control swatch is then determined by radiotracer methods, for example, by beta ray analysis and/or liquid scintillation counting.

Practice of the test method of the invention has led to a number of observations which aid in understanding the characteristics of soil redeposition during laundry. For instance, using the tests method of the invention, it has been found that redeposited soils do not build up on fabric surfaces over a number of wash cycles. Surprisingly, it is observed that in the course of the multiple wash cycles of the invention, the soil deposited on the control swatch after the first cycle is consistently less than that present on the swatch after five cycles.

It has also been found that, for detergent products containing a major amount of nonionic surfactant and lesser amounts of both anionic and cationic surfactants, optimal soil redeposition results (i.e., minimum soil redeposition) occurs when the anionic and cationic surfactants are present in equal molar quantities.

Applying the test method of the invention to a program for optimizing the composition of fabric softener containing detergent formulations in this regard, it has been found that compositions containing between about 80 and 90 percent by weight (% w) nonionic surfactant and between about 10 and 20% w anionic surfactant (where the % w values are on the basis of 100% w for the sum of the anionic plus nonionic components, only) are particularly effective when combined with any of a variety of known fabric softener components. For example, a most preferred nonionic/anionic surfactant combination is one containing as anionic about 13% w of $C_{12}$ linear alkyl benzene sodium sulfonate and as nonionic about 87% w of a $C_{12}$ to $C_{15}$ alcohol ethoxylate, for instance, a nine mole ethylene oxide adduct of a $C_{12}$ to $C_{15}$ alkanol mixture, (i.e., the addition product of an average of about 9 moles of ethylene oxide to one mole of a mixture of $C_{12}$ to $C_{15}$ predominantly linear alkanols). Another particularly preferred formulation is one which combines about 80% w of such alcohol ethoxylate with about 20% w of a $C_{12}$ to $C_{15}$ alcohol ethoxysulfate, for instance, the sodium sulfate salt of a three mole ethylene oxide adduct of a $C_{12}$ to $C_{15}$ alkanol mixture.

The invention is further illustrated by reference to the following examples.

EXAMPLE 1

Several detergent compositions were evaluated under the invention for removal and redeposition of mixed sebum (polar and nonpolar)/clay soil from permanent press polyester/cotton fabric.

Experiments were conducted in a Terg-O-Tometer, a device which is equipped with a beaker for containing detergent solution and fabric swatches and a constant-speed motor driven propeller for agitating the contents of the beaker.

In each experiment, one 4"×4" clean control cotton fabric swatch was placed in the Terg-O-Tometer, together with four 4"×4" fabric swatches presoiled with radiolabeled soil mixtures. The fabric weight of each swatch was 1.2 g. Each soiled swatch contained 5 mg of irradiated kaolinite clay and 28 mg of sebum with a composition which included the nonpolar components cetane (12.5% w), squalane (12.5% w) and tristeorin (10% w) and the polar components cholesterol (7% w), octadecanol (8% w), oleic acid (15% w), and stearic acid (15% w). Nonpolar sebum components of the sebum were labeled with $^3H$ and polar components with $^{14}C$. The kaolinite clay was made radioactive by neutron irradiation (Spinks Bandy Black). Published procedures (Journal of the American Oil Chemists' Society, vol. 46, no. 10, September 1976) were followed in labeling and soiling of the swatches with clay. The sebum soil was applied to the swatches after the clay as a solution of the several components in toluene. The toluene is evaporated from the soiled swatch before its use in the invention. Also added to the beaker were 500 ml water (150 ppm hardness) and either (1) a detergent formulation comprising 0.141 g of a nonionic surfactant or a combination of nonionic and anionic surfactants, 0.024 g of triethanolamine, and 0.028 g of fabric softener, or (2) a commercial detergent product in a quantity, relative to wash solution, approximating that recommended by the manufacturer for laundry service. The swatches were than washed, in a first wash cycle, at a temperature of 100° F. and an agitator speed of 100 rpm for 10 minutes. After the first cycle, the control swatch was removed from the wash mixture and air dried. The control swatch was then subjected to four further wash cycles in the Terg-O-Tometer under like conditions, each cycle in a fresh detergent solution and in the presence of four fresh soiled swatches.

Following completion of the five wash cycles, soil redeposition results are calculated in terms of percent soil redeposition, which is defined as the amount of soil deposited on the redeposition swatch divided by the total soil available for redeposition. Total soil available is the sum of that removed from the total of twenty soiled swatches during the five wash cycles and that deposited on the control swatch at the end of the fifth cycle. Analysis of the control swatch for soil deposition was performed by radiotracer methods. Soil remaining on the swatch was determined by beta and gamma emission counting, while soil removed was measured by scintillation counting of the wash solutions. The techniques were applied as described in the aforementioned publications, JAOCS, vol. 44, p. 289 and JAOCS vol. 46, p. 537.

Several detergent formulations were prepared, having the compositions indicated as follows for their nonionic and anionic surfactant component(s), and tested for soil redeposition properties. (NEODOL is a registered trademark for products marketed by Shell Chemical Company.) Several commercially available laundry detergent products were also tested.

formulation A—NEODOL 25-9, a nonionic surfactant characterized as the addition product of an average of 9 moles of ethylene oxide to one mole of a mixture of $C_{12}$ to $C_{15}$ predominantly linear alkanols;

formulation B—a mixture of equal parts by weight of the NEODOL 25-9 nonionic and a NEODOL 25-3S anionic surfactant characterized as the sulfate of the addition product of an average of 3 moles of ethylene oxide to one mole of a mixture of $C_{12}$ to $C_{15}$ predominantly linear alkanols;

formulation C—a mixture of equal parts by weight of NEODOL 25-9 nonionic and a $C_{12}$ linear alkylbenzene sulfonate (LAS) anionic;

formulation D—a first commercial laundry detergent product containing fabric softener;

formulation E—a second commercial laundry detergent product containing fabric softener;

formulation F—a third commercial laundry detergent product containing no fabric softener; and formulation G—a fourth commercial laundry detergent product containing fabric softener.

Each of formulations A, B and C contained Armosoft WAI04 fabric softener and also contained triethanolamine.

Each formulation was tested in duplicate experiments. The results of Example 1 are summarized in Table I.

TABLE I

| Formulation | Percent Soil Redeposition | |
|---|---|---|
| | Total Sebum (Polar + Nonpolar) | Clay |
| A | 0.25 | 0.21 |
| B | 0.13 | 0.08 |
| C | 0.13 | 0.07 |
| D | 0.24 | 0.14 |
| E | 0.17 | 0.12 |
| LSD | 0.05 | 0.04 |

LSD (Least Significant Difference between any two mean values at 95% confidence level) is a measure of the reliability of the test results.

For comparison, experiments were conducted not in accordance with the invention, to evaluate performance of a test method in which only two soiled swatches were washed with one control swatch for the five wash cycles. Comparative results, presented in Table 2, illustrate, in the form of higher LSD values, a substantially lower degree of reliability with the comparative test.

TABLE 2

| Formulation | Percent Soil Redeposition | |
|---|---|---|
| | Total Sebum (Polar + Nonpolar) | Clay |
| A | 0.24 | 0.12 |
| B | 0.12 | 0.08 |
| C | 0.43 | 0.24 |
| F | 0.15 | 0.12 |
| G | 0.42 | 0.26 |
| LSD | 0.37 | 0.33 |

EXAMPLE 2

The soil redeposition test method of the invention was applied to illustrate the dependence of the reliability of the results upon the number of wash cycles. The procedures of Example 1 were repeated, with the exception of the variation in the number of wash cycles. Three detergent formulations were tested, with compositions for nonionic and anionic surfactants as follows:

formulation A—as described in Example 1;

formulation H—a mixture of 80% w NEODOL 25-9 and 20% w NEODOL 25-3S, basis total weight of nonionic and anionic surfactants; and formulation I—a mixture of 87% w NEODOL 25-9 and 13% w LAS, basis total weight of nonionic and anionic surfactants. Each formulation contained the triethanolamine and the Armosolft WA104 fabric softener components at the indicated concentrations. Results are shown in Table 3, in terms of percent soil redeposition for total sebum, and in Table 4, in terms of percent soil redeposition for clay.

TABLE 3

| | Percent Soil Redeposition Number of Wash Cycles | | | | |
|---|---|---|---|---|---|
| Formulation | 1 cycle | 3 cycles | 5 cycles | 7 cycles | 10 cycles |
| D | 0.62 | 0.28 | 0.18 | 0.15 | 0.11 |
| H | 0.34 | 0.16 | 0.11 | 0.10 | 0.06 |
| I | 0.35 | 0.19 | 0.10 | 0.11 | 0.07 |
| LSD | 0.14 | 0.03 | 0.01 | 0.04 | 0.02 |

TABLE 4

| | Present Soil Redeposition Number of Wash Cycles | | | | |
|---|---|---|---|---|---|
| Formulation | 1 cycle | 3 cycles | 5 cycles | 7 cycles | 10 cycles |
| D | 0.54 | 0.24 | 0.16 | 0.12 | 0.12 |
| H | 0.25 | 0.16 | 0.08 | 0.11 | 0.06 |
| I | 0.30 | 0.14 | 0.06 | 0.10 | 0.07 |
| LSD | 0.57 | 0.12 | 0.09 | 0.07 | 0.04 |

EXAMPLE 3

The invention was applied using the procedures of Example 1 with the exception that the pre-soiled swatches were mineral oil and carbon black soiled polyester and cotton swatches obtained from Test Fabric Incorporated. The control swatch, also polyester/cotton, was evaluated before and after each test by reflectance techniques for percent whiteness retention; using the "y, x, z" Color Scale of the Gardiner XL-23 Tristimulus Colorimeter. Percent whiteness retention was calculated as the Y reflectance value of the washed control swatch (Yr) divided by the Y reflectance value of the clean control swatch (Yo), times 100. Detergent formulations tested each contained the triethanolamine and Armosoft WA104 components, and had the following nonionic and anionic surfactant composition:

formulations A, B, C and D—as described in Example 1;

formulations H and I—as described in Example 2;

formulation J—a mixture of 67% w NEODOL 25-9 and 33% w NEODOL 25-3S, basis total weight of nonionic and anionic surfactants; and formulation K—a mixture of 67% w NEODOL 25-9 and 33% w LAS, basis total weight of nonionic and anionic surfactants. Results are shown in Table 5, in terms of percent whiteness retention for duplicate tests. Yo for the control swatches was 83.64.

TABLE 5

| Formulation | Yr | % Whiteness Retention | Average % Whiteness Retention |
|---|---|---|---|
| A | 74.65 | 89.3 | 90.8 |
| | 77.26 | 92.4 | |
| H | 79.52 | 95.1 | 94.6 |
| | 78.80 | 94.2 | |
| J | 81.60 | 97.6 | 97.2 |
| | 80.91 | 96.7 | |
| B | 80.55 | 96.3 | 96.0 |
| | 80.02 | 95.7 | |
| I | 77.86 | 93.1 | 92.2 |
| | 76.37 | 91.3 | |
| K | 81.13 | 97.0 | 97.1 |
| | 81.30 | 97.2 | |
| C | 81.34 | 97.3 | 97.0 |
| | 80.97 | 96.8 | |
| D | 82.18 | 98.3 | 98.0 |
| | 81.78 | 97.8 | |
| LSD | | | 2.3 |

We claim as our invention:

1. A method for testing the performance of a detergent composition which comprises steps for
   a. washing in a first wash cycle and in a first soltuion of the detergent composition at least one clean control fabric swatch in the presence of a soiled fabric containing a total of at least about 150 mg soil per liter of said first solution,
   b. separating the control swatch from the first wash cycle,
   c. washing the control swatch in a second wash cycle and in a second solution of the detergent composition in the presence of soiled fabric containing a total of at least about 150 mg soil per liter of said second solution,
   d. separating the control swatch from second wash cycle, and
   e. measuring the soil content of the control swatch.

2. The test method of claim 1, wherein the control fabric swatch is separated from the second wash cycle, washed in at least one additional wash cycle and separated from the additional wash cycle, before soil content is measured in step (e).

3. The test method of claim 2, wherein the control fabric swatch is washed in a number of wash cycles in the range from 3 to 5.

4. The method of claim 3, wherein the soiled fabric present in each wash cycle contains a total of at least about 200 mg soil per liter of wash solution.

5. The method of claim 4, wherein the fabric swatches are cotton fabric or a polyester and cotton combination.

6. The method of claim 4, wherein the soiled fabric swatches are soiled with one or more radiolabeled soils and the content of soil on the control swatch is measured by radiotracer methods.

* * * * *